United States Patent [19]

Rao

[11] Patent Number: 5,136,113
[45] Date of Patent: Aug. 4, 1992

[54] CATALYTIC HYDROGENOLYSIS

[75] Inventor: V. N. M. Rao, Wilmington, Del.

[73] Assignee: E. I. Du Pont de Nemours and Company, Wilmington, Del.

[21] Appl. No.: 734,407

[22] Filed: Jul. 23, 1991

[51] Int. Cl.$^5$ .............................................. C07C 17/10
[52] U.S. Cl. .................................... 570/176; 570/153; 570/175
[58] Field of Search ........................ 570/176, 153, 175

[56] References Cited

U.S. PATENT DOCUMENTS

| | | | |
|---|---|---|---|
| 2,942,036 | 6/1960 | Smith et al. | 570/176 |
| 3,439,052 | 4/1969 | Bjornson. | |

FOREIGN PATENT DOCUMENTS

| | | | |
|---|---|---|---|
| 593529 | 3/1960 | Canada | 570/176 |
| 0347830 | 6/1989 | European Pat. Off. | |
| 3619079 | 6/1986 | Fed. Rep. of Germany. | |
| 1128942 | 5/1989 | Japan. | |
| 1578933 | 7/1977 | United Kingdom. | |

OTHER PUBLICATIONS

Augustine, "Catalytic Hydrogenation", p. 38.
Rylander, "Catalytic Hydrogenation Over Platinum Metals", p. 19.
Richardson, "Principles of Catalyst Development", p. 206.
A. A. Goleva et al., Russ J. Phys. Chem. 44, 290–1.
M. Biswas et al., J. Macromol. Sci Chem. A20(8), 861–76.
Ullmann's Encyclopedia of Industrial Chemistry, 5th ed., vol. A5, pp. 124–125.
Organic Synthesis, Collective vol. 3, pp. 685–690.
J. W. Hassler, "Activated Carbon", pp. 344–345.
M. Smisek et al., "Active Carbon", pp. 61–70.
F. J. Long et al., "The Effect of of Specific Catalysts on the Reactions of the Steam–Carbon System", Proc. Roy. Soc. (1952) pp. 100–110.
F. J. Long et al., "The Catalysis of the Oxidation of Carbon", J. Chem. Phys. 47, pp. 361–378 (1950).
R. B. Anderson et al., "Surface Complexes on Charcoal", J. Phys. Colloid. Chem., 51, pp. 1308–1329.
H. M. Frey, "A New Type of Catalytic Effect in the Oxidation of Carbon", Proc. Roy. Soc. (1055) pp. 510–518.

Primary Examiner—Alan Siegel

[57] ABSTRACT

Catalytic hydrogenolysis of fluorohalocarbons (e.g., CFCs) and fluorohalohydrocarbons (e.g., HCFCs), using catalysts of Re, Co, Ni, Ru, Rh, Pd, Os, Ir, and/or Pt on a carbon having low ash content. Preferred catalysts use carbon which is acid-washed, first with an acid other than hydrofluoric acid and then with hydrofluoric acid; and also have a low content of phosphorus, sulfur, potassium, sodium and iron.

20 Claims, No Drawings

CATALYTIC HYDROGENOLYSIS

BACKGROUND OF THE INVENTION

1. Field of the Invention

This invention relates to the catalytic hydrogenolysis of fluorohalocarbons or fluorohalohydrocarbons and more particularly to carbon supported Group VII or Group VIII metal catalysts and their use in the hydrogenolysis of fluorohalccarbons or fluorohalohydrocarbons.

2. Background

A number of chlorinated fluorocarbons are considered to be detrimental toward the Earth's ozone layer. There is a world-wide effort to develop materials that can serve as effective replacements. For example, 1,1,1,2-tetrafluoroethane (HFC-134a), a fluorohydrocarbon containing no chlorine, is being considered as a replacement for dichlorodifluoromethane (CFC-12) in refrigeration systems because of its zero ozone depletion potential. There is thus a need for manufacturing processes that provide fluorocarbons that contain less chlorine.

One method of reducing the chlorine content of halogen substituted hydrocarbons containing chlorine as well as fluorine is reacting organic starting materials containing chlorine and fluorine with hydrogen at elevated temperature in the presence of a hydrogenation catalyst (e.g., supported Group VII or Group VIII metal catalysts). British Patent Specification 1,578,933 discloses, for example, that HFC-134a can be prepared by the hydrogenolysis of 2,2-dichloro-1,1,1,2-tetrafluoroethane (CFC-114a) or 1,1,1,2-tetrafluorochloroethane (HCFC-124) over palladium on carbon or palladium on alumina hydrogenation catalysts. There remains a continued interest in providing improved hydrogenolysis processes for the manufacture of HFC-134a as well as other fluorohydrocarbons and fluorohalohydrocarbons.

Techniques for enhancing the activity of Group VIII metal hydrogenolysis catalysts have been disclosed. The catalyst improvements described in Eur. Pat. Appln. 347,830 and Jap. Pat. Appln. 1-128,942 are achieved by the addition of other elements, such as Group IB, lanthanum, lanthanide elements, and rhenium to the Group VIII metal catalysts. The additives are said to prevent sintering and also increase the activity and the mechanical strength of the catalysts.

Palladium catalysts are considered generally to be resistant to catalyst poisons (Augustine, "Catalytic Hydrogenation" Marcel Dekker, inc., N.Y, 1965, page 38); although Rylander "Catalytic Hydrogenation over Platinum Metals," Academic Press, New York, 1967, p. 19, reveals that all types of metal cations may cause drastic inhibition of platinum metal catalysts. However, there is no way of generalizing what the effect of any particular cation will be. Furthermore ions such as $Na^+$, $K^+$, and $Ca^{2+}$ have been reported to be nontoxic to platinum (J. T. Richardson, "Principles of Catalyst Development," Plenum Press, New York, 1989, P. 206) and in view of the above are considered to be non-toxic toward palladium.

U.S. Pat. No. 2,942,036 claims a process for hydrogenating 1,2,2-trichloropentafluoropropane over a palladium supported on activated carbon catalyst. The carbon support may be treated prior to depositing palladium on it with aqueous HF. The purpose of this treatment is to remove any silica from the carbon.

Various processes using catalysts containing acid-washed carbon have been studied. A. A. Goleva et al., Russ. J. Phys. Chem., 44², 290–1 (1970) disclose the dehydrochlorination of 1,1,2,2-tetrachlorethane to trichloroethylene and HCl using activated charcoal as the catalyst. Activated charcoal treated with hydrochloric acid proved to be more active than an untreated specimen for the production of the olefin, trichloroethylene. M. Biswas et al, J. Macromol. Sci., Chem., A20(8), 861–76 (1983) disclose that the activity of carbon black catalysts for the polymerization of N-vinylcarbazole can be enhanced by treatment with protonic acids such as $HNO_3$, $H_2SO_4$ and $HClO_4$. Chem. Abst. 80 (25): 145470q and Chem. Abst. 80 (25): 145469w disclose an increase in yields of unsaturated glycol diesters when the active carbon catalyst support was treated with HN03 compared with untreated carbon.

SUMMARY OF THE INVENTION

This invention provides a process for the catalytic hydrogenolysis of fluorohalocarbons and fluorohalohydrocarbons using a catalyst of at least one metal selected from the group consisting of rhenium, cobalt, nickel, ruthenium, rhodium, palladiux osmium, iridium, and platinum supported on carbon, which is characterized by the carbon support having an ash content of less than about 0.1% by weight (based on the weight of said support). Suitable hydrogenolysis catalysts may be prepared by treating a carbon support with acid other than hydrofluoric acid (e.g., hydrochloric acid), and then treating the acid washed carbon support with hydrofluoric acid, washing said support with deionized water, drying said support, and depositing a catalyst precursor (e.g., pallatium chloride) on said support.

The process of this invention is considered particularly useful for the conversion of 2,2-dichloro-1,1,1,2-tetrafluoroethane (CFC-114a) to 2-chloro-1,1,1,2-tetrafluoroethane (HCFC-124) and 1,1,1,2-tetrafluoroethane (HFC-134a), and HCFC-124 to HFC-134a.

DETAILS OF THE INVENTION

This invention provides a process for the catalytic hydrogenolysis of fluorohalocarbons and fluorohalohydrocarbons using a low ash content carbon supported catalyst containing at least one metal selected from the group consisting of rhenium, cobalt, nickel, ruthenium, rhodium, palladium, osmium, iridium and platinum. In accordance with this invention, the carbon support of the catalyst used for hydrogenolysis contains less than about 0.1 weight percent ash.

The fluorohalocarbons and/or fluorohalohydrocarbons used in the hydrogenolysis reactions of this invention are preferably those wherein halo is chloro or bromo. Included are fluorohalocarbons consisting of carbon, fluorine and at least one of chlorine and bromide; and fluorohalohydrocarbons, consisting of carbon, fluorine, hydrogen, and at least one of chlorine and bromine. Hydrogenolysis of chlorofluorocarbons (i.e., CFCs) and hydrochlorofluorocarbons, (i.e., HCFCs) is thus provided by this invention. Suitable fluorohalocarbons and fluorhalohydrocarbons may contain 1 to 6 carbon atoms, and include the cyclic as well as acyclic compounds represented by the empirical formula $C_nH_mF_pX_q$, wherein each X is independently selected from Cl and Br, and iS preferably Cl, and wherein n is an integer from 1 to 6, m is an integer from 0 to 12, p is an integer from 1 to 13, and q is an integer from 1 to 13, provided that $m+p+q$ equals $2n+2$ when the compound is saturated and acyclic, equals $2n$ when the compound is saturated and cyclic or is olefinic and acyclic, and equals $2n-2$ when the compound is olefinic and cyclic. The hydrogenolysis process produces predominantly saturated products.

Preferred applications include hydrogenolysis of compounds containing 1 to 3 carbon atoms. Examples of acyclic compounds which undergo hydrogenolysis include 1,1,1,2-tetrachloro-2,2-difluoroethane (CFC-112a), which may be hydrogenolyzed to 1,1-difluoroethane (HFC-152a); 1,1,2-trichloro-1,2,2-trifluoroethane (CFC-113) which trifluoethane (HCFC-123a); 1,1,1-trichloro-2,2,2-trifluoroethane (CFC-113a) which may be hydrogenolyzed to 2,2,-dichloro-1,1,1,-trifluoroethane (HCFC-123); 1,2-dichloro-1,1,2,2-tetrafluoroethane (CFC-114) which may be hydrogenolyzed to 1-chloro-1,1,2,2-tetrafluoroethane (HCFC-124a) and 1,1,2,2,-tetrafluoroethane (HFC-134); 2,2-dichloro-1,1,1,2-tetrafluoroethane (CFC-114a), which may be hydrogenolyzed to 2-chloro-1,1,1,2-tetrafluoroethane (HCFC-124) and 1,1,1,2-tetrafluoroethane (HFC-134a); and HCFC-124 itself which may be hydrogenolyzed to HFC-134a. Examples of cyclic compounds include 4,5-dichloro-1,1,2,2,3,3-hexafluorocyclopentane which may be hydrogenolyzed to 1,1,2,2,3,3-hexafluorocyclopentane.

In a preferred embodiment the fluorohalocarbons and/or fluorhalohydrocarbons are represented by the above empirical formula where n is 1 to 3, m is 0 to 6, p is 1 to 7, and q is 1 to 7.

In accordance with this invention the fluorohalocarbon(s) and/or fluorohalohydrocarbon(s) to be hydrogenolyzed are reacted with hydrogen at an elevated temperature in the presence of the low ash content carbon supported catalysts disclosed herein. The reaction is suitably carried out at a temperature which is at least about 125° C. Typically temperatures are about 350° C. or less. Preferred temperatures depend to some extent upon the particular fluorohalocarbons(s) and/or fluorohalohydrocarbon(s) to be reacted.

A conventional amount of $H_2$ is used. Generally, in order to provide substantial hydrogenolysis product yields, the amount of hydrogen used is at least about 0.5 moles per mole of fluorohalocarbon and/or fluorohalohydrocarbon used. To provide yields desired in many embodiments, at least stoichiometric amounts of hydrogen are used.

The hydrogenolysis of fluorohalocarbons or fluorohydrohalocarbons can be performed in liquid-phase or vapor-phase using well-known chemical engineering practice, which includes continuous, semi-continuous or batch operations. The hydrogenolysis process is typically achieved at atmospheric or superatmospheric pressures.

In accordance with this invention, supported catalysts suitable for hydrogenolysis are provided which contain at least one metal selected from the group consisting of rhenium, cobalt, nickel, ruthenium, rhodium, palladium, osmium, iridium and platinum. Said metal component is supported on carbon and typically constitutes between about 0.1 and 10 percent by weight of the catalyst.

Suitable catalysts may be prepared by treating the carbon used as catalyst support with two acids. Typically the support is then washed with deionized water and dried; and the metal is then deposited thereon using deposit techniques well known in the art (e.g., using a catalyst precursor such as palladium chloride). The first acid treatment uses an acid other than hydrofluoric acid. Preferably the acid used for the first acid treatment contains neither phosphorus nor sulfur. The second acid treatment uses hydrofluoric acid. The carbon is treated with acid such that after such treatment the carbon contains less than about 0.1% by weight ash. Preferably, after such treatment and the subsequent deposit of the metal component, the catalyst also contains less than about 200 ppm phosphorus and less than about 200 ppm sulfur; more preferably less than 100 ppm phosphorus and less than 100 ppm sulfur; and most preferably less than 50 ppm phosphorus and less than 50 ppm sulfur. The preferred catalysts of this invention also contain less than about 100 ppm potassium. Washing the carbon with an acid which provides removal of excess potassium as well as phosphorus and sulfur is thus particularly preferred. Most preferably the catalyst of this invention contain less than about 100 ppm sodium and/or less than about 100 ppm iron. Accordingly, washing with acids that remove excess sodium and iron is especially preferred. Reference is made to U.S. patent application Ser. No. 7/633,922 which is hereby incorporated herein in its entirety, for further discussion of advantageous use of carbon supported catalysts having a low content of phosphorus, sulfur, potassium, sodium and/or iron. Commercially available carbons which may be treated with acids to provide suitable supports include those sold under the following trademarks: Darco TM, Nuchar TM, Columbia SBV TM, Columbia MBV TM, Columbia MBQ TM, Columbia JXC TM, Columbia CXC TM, Calgon PCB TM, and Barnaby Cheny NB TM. The carbon support can be in the form of powder, granules, or pellets, etc.

Examples of acids which may be used in the first acid wash during the catalyst preparation process include organic acids such as acetic acid and inorganic acids, e.g., HCl or $HNO_3$. Preferably hydrochloric acid or nitric acid is used. The acid treatment may be accomplished in several ways. A preferred embodiment is described below.

A carbon support is soaked overnight with gentle stirring in a 1 molar solution of the acid prepared in deionized water. The carbon support is then separated and washed at least 10 times with deionized water or until the pH of the washings is about 3. (Preferably, the carbon support is then soaked again with gentle stirring in a 1 molar solution of the acid prepared in deionized water for 12 to 24 hours.) The carbon support is then finally washed with deionized water until the washings are substantially free of the anion of the acid (e.g., Cl— or $NO_3-$), when tested by standard procedures. The carbon support is then separated and dried at 120° C. The washed carbon is then soaked in 1 molar HF prepared in deionized water for 48 hours at room temperature with occasional stirring (e.g., in a plastic beaker). The carbon support is separated and washed repeatedly with deionized water at 50° C. until the pH of the washings is greater than 4. The carbon support is then dried at 150° C. for 60 hours in air followed by calcination at 300° C. for 3 hours in air prior to its use as a support.

Practice of the invention will become further apparent from the following non-limiting examples.

EXAMPLES

Preparation of HCl-Washed Carbon

A commercially available carbon (500 g, Engelhard 6×16 mesh granules) was soaked for 120 hours with gentle stirring in IM HCl. The carbon granules were collected on a fritted glass funnel and washed with deionized water (422 L) until the washings were chloride free when tested with silver nitrate. Finally the carton granules were dried at 120° C. for 60 hours followed by calcination at 300° C. in air to obtain 468.8 g of dried calcined granules. The ash content and various elements present in the ash before and after acid washing are shown in Table I under NAW and ClW, respectively.

Preparation of HF-Washed Carbon

The commercially available carbon used for preparation of the HCl-washed carbon (225 g, 6×16 mesh granules) was soaked for 48 hours at room temperature with occasional stirring in IM HF (3 L) in a plastic jug. The carbon granules were then placed in a 4 L plastic beaker on a steam bath and washed with deionized water (3 L portions, 30 min. soak) until the washings had a pH greater than 4.0 (114 L). Finally the carbon granules were dried at 125° C. for 60 hours in air to obtain 212.9 g of dried granules. The ash content and various elements present in the ash are shown in Table I under FW.

Preparation of HCl/HF-Washed Carbon

HCl-washed carbon (225 g, 6×16 mesh granules) prepared as described above was soaked for 48 hours at room temperature with occasional stirring in IM HF (3 L] in a plastic jug. The carbon granules were then placed in a 4 L plastic beaker on a steam bath and washed with deionized water (3 L portions, at about 50° C.) until the washings had a pH greater than 4.0 (114 L). Finally the carbon granules were dried at 150° C. for 60 hours in air followed by calcination at 300° C. in air for three hours to obtain 216.6 g of dried calcined granules. The ash content and various elements present in the ash are shown in Table I under ClFW.

Preparation of Water-Washed Carbon

The commercially available carbon used above for preparation of the HCl-washed carbon (200 g, 6×16 mesh granules) was soaked for 68 hours at room temperature with occasional stirring in deionized water in a 3 liter beaker. The carbon granules were collected on a fritted glass funnel and washed 10× with deionized water by soaking the granules in 1 liter of deionized water for 15 minutes at room temperature. Finally the carbon granules were dried at 120° C. for 48 hours in air to obtain 189.9 g of dried calcined granules. The ash content and various elements present in the ash are shown in Table I under WW.

TABLE I

| | Elemental Analysis of Carbon Granules | | | | |
|---|---|---|---|---|---|
| | ClW[a] (ppm) | FW[b] (ppm) | ClFW[c] (ppm) | WW[d] (ppm) | NAW[e] (ppm) |
| P | | | | | 320 |
| S | | | | | 3200 |
| Si | 760 | 215 | 74 | 1200 | 905 |
| Cu | 18 | 9 | 3 | 20 | 12 |
| Mn | 1 | 4 | <1 | 17 | 11 |
| Fe | 65 | 75 | 25 | 120 | 90 |
| Ba | <1 | 3 | | 11 | 7 |
| Ca | 17 | 175 | | 715 | 755 |
| Zn | <3 | <5 | <1 | 195 | 5 |
| Mg | 21 | 90 | | 530 | 540 |
| K | 28 | <45 | | 1000 | 7300 |
| Al | <240 | | | | <120 |
| Na | 250 | 79 | | 140 | 465 |
| Ti | <30 | | 12 | | 6 |
| Ash | 0.18% | 0.21% | 0.01% | 0.55% | 2.33% |

[a]HCl washed (used to prepare Catalyst B)
[b]HF washed (used to prepare Catalyst C)
[c]HCl and HF washed (used to prepare Catalyst D)
[d]water-washed (used to prepare Catalyst E)
[e]not acid-washed (used to prepare Catalyst A)

EXAMPLE 1

Hydrogenolysis of CF$_3$CCl$_2$F (CFC-114a) and CF$_3$CHClF (HCFC-124)

Four different 0.5% Pd/C catalysts were prepared and used to catalyze the hydrogenolysis of CFC-114a to HCFC-124 and CF$_3$CH$_2$F (HFC-134a), and the hydrogenolysis of HCFC-124 to HFC-134a. The results of experiments using these four catalysts are shown in Tables II and III.

Catalyst A 0.5% Pd on Non-Acid-Washed (NAW) Carbon

Commercial carbon (100 g, 6×16 mesh granules) was added to a solution of palladium chloride (0.84 g) in conc. hydrochloric acid (2 mL) and deionized water (160 mL). The slurry was then stirred occasionally at room temperature for one hour. It was then dried with frequent stirring at 150° C. for 18 hours in air to obtain 102.2 g of 0.5% Pd on carbon.

A sample (96.7 g) of the above dried catalyst was placed in a quartz boat under a helium flow of 100 cc/min. for 15 minutes at room temperature. The catalyst was then heated as follows: 150° C./1 hr./helium (100 cc/min.); 150° C./1 hr./helium (100 cc/min.)-hydrogen (100 cc/min.); 300° C./8 hr./helium (100 cc/min.)-hydrogen (100 cc/min.). The hydrogen flow was stopped; the catalyst was maintained at 300° C. in helium (100 cc/min.) for ½ hr. followed by cooling in helium. Finally the catalyst was passivated with 1.5% oxygen in nitrogen at room temperature for ½ hour.

Catalyst B 0.5% Pd on HCl-Washed (ClW1 Carbon

A portion of (100 g) of HCl-washed carbon prepared as described above was added to a solution of palladium chloride (0.84 g) in conc. hydrochloric acid (2 mL) and deionized water (160 mL). The slurry was then stirred occasionally at room temperature for one hour. It was then dried with frequent stirring at 150° C. for 18 hours in air to obtain 102.0 g of 0.5% Pd on carbon.

A sample (96.4 g) of the above dried catalyst was placed in a quartz boat under a helium flow of 100 cc/min. for 15 minutes at room temperature. The catalyst was then heated as follows: 150° C./1 hr./helium (100 cc/min.); 150° C./1 hr./helium (100 cc/min.)-hydrogen (100 cc/min.); 300° C./8 hr./helium (100 cc/min.)-hydrogen (100 cc/min.). The hydrogen flow was stopped; the catalyst was maintained at 300° C. in helium (100 cc/min.) for ½ hr. followed by cooling in helium. Finally the catalyst was passivated with 1.5% oxygen in nitrogen at room temperature for ½ hour.

Catalyst C

0.5% Pd on HF-Washed (FW) Carbon

A portion of (200 g) of HF-washed carbon prepared as described above was added to a solution of palladium chloride (1.67 g) in conc. hydrochloric acid (4.0 mL) and deionized water (320 mL). The slurry was then stirred occasionally at room temperature for two hours. It was then dried with frequent stirring at 150° C. for 18 hours in air to obtain 203.0 g of 0.5% Pd on carbon.

A sample (101.5 g) of the above dried catalyst was placed in a quartz boat under a helium flow of 100 cc/min. for 15 minutes at room temperature. The catalyst was then heated as follows: 150° C./1 hr./helium (100 cc/min.); 150° C./1 hr./helium (100 cc/min.)-hydrogen (100 cc/min.); 300° C./8 hr./helium (100 cc/min.)-hydrogen (100 cc/min.). The hydrogen flow was stopped; the catalyst was maintained at 300° C. in helium (100 cc/min.) for ½ hr. followed by cooling in helium. Finally the catalyst was passivated with 1.5% oxygen in nitrogen at room temperature for ½ hour.

Catalyst D

0.5% Pd on HCl/HF-Washed (ClFW) Carbon

A portion of (100 g) of HCl/HF-washed carbon prepared as described above was added to a solution of palladium chloride (0.84 g) in conc. hydrochloric acid (2.0 mL) and deionized water (160 mL). The slurry was then stirred occasionally at room temperature for two hours. It was then dried with frequent stirring at 0° C. for 18 hours in air to obtain 101.7 g of 0.5% Pd on carbon.

A sample (97.4 g) of the above dried catalyst was placed in a quartz boat under a helium flow of 100 cc/min. for 15 minutes at room temperature. The catalyst was then heated as follows: 150° C./1 hr./helium (100 cc/min.); 150° C./1 hr./helium (100 cc/min.)-hydrogen (100 cc/min.); 300° C./8 hr./helium (100 cc/min.)-hydrogen (100 cc/min.). The hydrogen flow was stopped; the catalyst was maintained at 300° C. in helium (100 cc/min.) for ½ hr. followed by cooling in helium. Finally the catalyst was passivated with 1.5% oxygen in nitrogen at room temperature for ½ hour.

Catalyst E

0.5% Pd on Water-Washed (WW) Carbon

A portion of (175 g) of water-washed carbon prepared as described above was added to a solution of palladium chloride (1.46 g) in conc. hydrochloric acid (3.5 mL) and deionized water (280 mL). The slurry was then stirred occasionally at room temperature for two hours. It was then dried with frequent stirring at 150° C. for 18 hours in air to obtain 177.3 g of 0.5% Pd on carbon.

A sample (88.7 g) of the above dried catalyst was placed in a quartz boat under a helium flow of 100 cc/min. for 15 minutes at room temperature. The catalyst was then heated as follows: 150° C./1 hr./helium (100 cc/min.); 150° C./1 hr./helium (100 cc/min.)-hydrogen (100 cc/min.); 300° C./8 hr./helium (100 cc/min.)-hydrogen (100 cc/min.). The hydrogen flow was stopped; the catalyst was maintained at 300° C. in helium (100 cc/min.) for ½ hr. followed by cooling in helium. Finally the catalyst was passivated with 1.5% oxygen in nitrogen at room temperature for ½ hour.

General Procedure for Catalyst Evaluation

A 6" × ½" O. D. Hastelloy ™ C nickel alloy reactor was charged with the catalyst (5.0 g) for evaluation. The reactor contents were heated to a temperature of 175° C. over a period of five hours, during which time an equimolar flow, 10 cc/min each, of nitrogen and hydrogen was passed through the reactor. At the end of this five hour period, nitrogen flow was stopped, the hydrogen flow increased to 20 cc/min, the reactor temperature raised to 275°C. over a 2 ½ hour period and maintain at this temperature for an additional 16 hours. After this period, the reactor temperature was decreased to the desired operating temperature for catalyst evaluation.

General Procedure for Product Analysis

The products leaving the reactor were analyzed on line using a gas chromatograph. The column consisted of a 20′ × ⅛″s/s tube containing Krytox ™ perfluorinated polyether on an inert support. Helium was used as the carrier gas. The product analyses are reported in area percent and are shown in Table II for CFC-114a hydrogenolysis and in Table III for HCFC-124 hydrogenolysis. The first numbers in each table are for a run time of about 5.5 hours, the second numbers represent analysis for a run time of about 26 hours.

The CFC-114a hydrogenolysis was done under the following conditions: temperature —150° C., pressure —atmospheric, [$H_2$]/[CFC-114]=2, total flow =30 cc/min., and the results are shown in Table II. The HCFC-124 hydrogenolysis was done under the following conditions: temperature —250° C., pressure —atmospheric, [$H_2$]/]HCFC-124]=1, total flow=20 cc/min., and the results are shown in Table III.

TABLE II

| | $CF_3CCl_2F \rightarrow CF_3CHClF + CF_3CH_2F$ | | | | |
|---|---|---|---|---|---|
| Cat. Prep. | % 114a[a] Conv. | % Sel. to 124[b] | % Sel. to 134a[c] | % Sel. to 143a[d] | % Sel. to 124 + 134a |
| A (NAW) | 22.9 | 14.6 | 72.3 | 13.1 | 86.9 |
| | 23.0 | 12.0 | 74.0 | 14.0 | 86.0 |
| B (ClW) | 45.3 | 16.7 | 79.8 | 3.5 | 96.5 |
| | 46.2 | 13.6 | 82.5 | 3.9 | 96.1 |
| C (FW) | 53.0 | 14.1 | 80.9 | 5.1 | 94.9 |
| | 49.2 | 11.8 | 83.1 | 5.1 | 94.9 |
| D (ClFW) | 51.9 | 16.8 | 81.6 | 1.6 | 98.4 |
| | 52.9 | 11.0 | 87.0 | 2.0 | 98.0 |
| E (WW) | 28.2 | 18.4 | 70.1 | 11.5 | 88.5 |
| | 25.6 | 15.9 | 72.2 | 12.0 | 88.0 |

[a]114a = CFC-114a = $CF_3CCl_2F$
[b]124 = HCFC-124 = $CF_3CHClF$
[c]134a = HFC-134a = $CF_3CH_2F$
[d]143a = HFC-143a = $CF_3CH_3$

Examination of the results in Table II shows that both 114a conversion (Conv.) and selectivity (Sel.) to 124 plus 134a are increased relative to Catalyst Preparation A using catalysts prepared from washed carbon supports and that the highest 114a Conv. and Sel. to 124 plus 134a are obtained from Catalyst Preparation D.

TABLE III

| | $CF_3CHClF \rightarrow CF_3CH_2F$ | | |
|---|---|---|---|
| Cat. Prep. | % 124 Conv. | % Sel. to 134a | % Sel. to 143a |
| B (ClW) | 47.4 | 92.4 | 7.6 |
| | 47.7 | 94.2 | 5.8 |

TABLE III-continued

| | CF₃CHClF → CF₃CH₂F | | |
|---|---|---|---|
| Cat. Prep. | % 124 Conv. | % Sel. to 134a | % Sel. to 143a |
| C (FW) | 39.9 | 92.2 | 7.9 |
| | 39.6 | 93.8 | 6.2 |
| D (ClFW) | 50.5 | 94.3 | 6.7 |
| | 50.7 | 95.5 | 4.5 |

Examination of the results in Table III shows that the highest 124 Conv. and Sel. to 134a are obtained over the catalyst with the lowest ash content, Catalyst Preparation D.

Particular embodiments of the invention are included in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but is embraces such modified forms thereof as come within the scope of the claims.

What is claimed is:

1. A process for the catalytic hydrogenolysis of a cyclic or acyclic compound having the formula $C_nH_mF_pX_q$ wherein n is an integer from 1 to 6, m is an integer from 0 to 12, p is an integer from 1 to 13, q is an integer from 1 to 13 and each X is independently selected from Cl and Br, provided that $m+p+q$ equals $2n+2$ when the compound is saturated and acyclic, equals $2n$ when the compound is saturated and cyclic or is olefinic and acyclic, and equals $2n-2$ when the compound is olefinic and cyclic, using a catalyst of at least one metal selected from the group consisting of rhenium, cobalt, nickel, ruthenium, rhodium, palladium, osmium, iridium and platinum supported on carbon which is characterized by the carbon support having an ash content of less than about 0.1 percent by weight.

2. The process of claim 1 wherein the carbon support is first treated with acid other than hydrofluoric acid and then treated with hydrofluoric acid.

3. The process of claim 2 wherein the first acid treatment uses acid containing neither phosphorus nor sulfur.

4. The process of claim 2 wherein the first acid treatment uses HCl or HNO₃.

5. The process of claim 1 wherein each X is Cl.

6. The process of claim 5 wherein the catalyst contains less than 200 ppm phosphorus.

7. The process of claim 5 wherein the catalyst contains less than 200 ppm sulfur.

8. The process of claim 5 wherein the catalyst contains less than 100 ppm potassium.

9. The process of claim 8 wherein the catalyst contains less than 100 ppm sodium.

10. The process of claim 9 wherein the catalyst contains less than 100 ppm iron.

11. The process of claim 1 wherein n is 1 to 3, m is 0 to 6, p is 1 to 7 and q is 1 to 7.

12. The process of claim 1 wherein said at least one metal constitutes between about 0.1 and 10 percent by weight of the catalyst.

13. The process of claim 1 wherein hydrogenolysis is carried out at a temperature between about 125° C. and about 350° C.

14. The process of claim 1 wherein 2,2-dichloro-1,1,1,2-tetrafluoroethane is converted to 2-chloro-1,1,1,2-tetrafluoroethane and 1,1,1,2-tetrafluoroethane.

15. The process of claim 1 wherein 2-chloro-1,1,1,2-tetrafluoroethane is converted to 1,1,1,2-tetrafluoroethane.

16. The process of claim 1 wherein the catalyst contains less than 100 ppm potassium.

17. The process of claim 1 wherein the catalyst contains less than 100 ppm sodium.

18. The process of claim 1 wherein the catalyst contains less than 100 ppm iron.

19. The process of claim 1 wherein the catalyst contains less than 200 ppm phosphorus.

20. The process of claim 1 wherein the catalyst contains less than 200 ppm sulfur.

* * * * *